United States Patent [19]
Hyde et al.

[11] Patent Number: 4,615,866
[45] Date of Patent: Oct. 7, 1986

[54] FLUID-SAMPLING SYSTEM AND METHOD

[75] Inventors: David D. Hyde, Camby; James R. Stuart, Sheridan, both of Ind.

[73] Assignee: American Monitor Corporation, Indianapolis, Ind.

[21] Appl. No.: 635,295

[22] Filed: Jul. 27, 1984

[51] Int. Cl.⁴ .............................................. G05D 9/00
[52] U.S. Cl. ...................................... 422/106; 436/43
[58] Field of Search ............................. 436/43, 63–67; 222/638, 639, 642, 643, 644, 251, 255, 263; 422/105, 106

[56] References Cited

U.S. PATENT DOCUMENTS

| | | | |
|---|---|---|---|
| 3,901,656 | 8/1975 | Durkos et al. | 23/230 B |
| 4,429,584 | 2/1984 | Beyer et al. | 422/64 |

*Primary Examiner*—Frank Sever
*Attorney, Agent, or Firm*—Willian Brinks Olds Hofer Gilson & Lione

[57] ABSTRACT

Fluid-sampling system and method for automated, chemistry-analyzing apparatus for withdrawing precise quantities of serum samples from a specimen container and for dispensing the samples into reagent containers for analysis. The apparatus includes a sampler assembly coupled to pressure-generating means for the withdrawal and dispensing of the serum by the sampler assembly. The system is designed such that the quantity of a serum sample taken up and dispensed will be a function only of the fluid mechanics of the sampling system and the timed operation of a control valve rather than being a function of any pressure variations established in the flow control means as in prior systems. This permits infinitely variable, very small, yet very precise quantities of a serum or other fluid to be taken up and dispensed permitting more efficient and cost effective use of available serum. The apparatus further includes means for simultaneously withdrawing more than one sample of a particular serum from a serum specimen container for permitting more than one test to be initiated on a particular serum during a single cycle of the chemistry-analyzing apparatus. Serum-level detecting means are also provided to ensure that the sampler assembly is properly immersed in a serum specimen before the pressure-generating means is actuated to withdraw serum therefrom. A microprocessor controller is provided to control the overall operation of the fluid-sampling system.

37 Claims, 4 Drawing Figures

FLUID-SAMPLING SYSTEM AND METHOD

BACKGROUND OF THE INVENTION

The present invention relates generally to an improved fluid-sampling system and method and, more particularly, to a method and apparatus for taking serum samples, such as samples of blood, spinal fluid, or the like, and placing them in chemical reagents for analysis.

The chemical analysis of a serum, for example, for the presence of sugar, albumin, or some other medically significant factor, is a vital part of medical diagnosis. Testing for various serum constituents is typically accomplished by combining a sample of the serum with one or more specific reactive chemicals or reagents and, after all chemical reactions are completed, by determining the light transmittance value of the completed test chemistry with a spectrophotometer or the like. The light transmittance value is used to calculate the optical density of the test chemistry and to derive the percentage concentration in the serum of the constituent of interest.

In performing a serum analysis, it is desirable to use the smallest possible quantity of serum for each particular test being undertaken. In many cases, only a very small amount of serum is available for the test; for example, spinal fluid specimens or blood specimens from pediatric or geriatric patients. In other cases, it is desirable to perform a number of different tests on a particular serum specimen; and it is necessary that there be enough of the serum available to conduct all of the tests. Also, the greater the quantity of serum used for a particular test, the greater the quantity of the reagents that must be used; and since many reagents are quite expensive, this can significantly increase the overall cost of the analysis.

At the present time, a large portion of the serum analyses being conducted are performed by automated systems. In performing such tests, it is essential that precise quantities of the serum and the appropriate reagents for the tests be mixed together in the correct proportions to ensure an accurate result when the test chemistry is analyzed. Most automatic systems currently on the market, however, are simply not able to achieve this necessary precision when only a very small quantity of a serum is used. Thus, notwithstanding the desirability of using the smallest possible quantity of a serum sample in each test, most automated systems currently in use are severely limited by the accuracy and precision of the measuring or metering means used in the system.

An automatic chemistry-analyzing system is disclosed, for example, in commonly assigned U.S. Pat. No. 3,901,656. In commonly assigned, co-pending U.S. patent application Ser. No. 304,384 filed on Sept. 22, 1981, and entitled ULTRA MICRO PRECISION FLUID METERING DEVICE, an automatic chemistry analyzer is disclosed that describes the use of a Bourdon pump to withdraw liquid from a first container as a sample having a definite size and to dispense the sample into a second container. More specifically, the Bourdon pump in the above-identified patent application is designed to provide samples in preselected increments of size. The size of the sample is determined by energizing one or more of a plurality of chambers of differing sizes by exerting pressure upon a surface of one or more of the chambers, and the sizes of the samples available are fixed by the sizes of the chambers built into the pump.

In many automated systems, a plurality of serum specimens are supported in individual containers on a turntable or other conveyor means; and a sample of the specimen to be tested is taken from the appropriate container by a sampler assembly when that container is in the proper transfer position relative to the sampler assembly. If it is desired to perform two tests on a particular serum, it is usually necessary to wait until the conveyor means has returned that particular serum specimen to the transfer position so that a second sample of the serum can be taken from the container.

SUMMARY OF THE INVENTION

In accordance with the invention, a fluid-sampling system for an automated chemistry-analyzing apparatus is provided which permits very small, yet precisely measured amounts of a serum sample to be taken from a specimen container for the purpose of being combined with appropriate reagents for testing of the serum.

The sampling system of the invention employs pressure-generating means in an arrangement that provides both a positive and a negative pressure to produce a very precisely controllable flow in both directions in the fluid-sampling system to permit a very precise amount of a serum to be taken from the specimen container and dispensed into or combined with the appropriate reagents for the particular test being conducted.

The system of the invention permits infinitely variable and very small sample quantities to be taken up and dispensed. The pressure-generating means, preferably a Bourdon pump, produces a substantially constant positive or negative pressure; and the sample quantity to be taken up and dispensed is determined by the fluid mechanics of the sampling system and its effect on flow rate, and the timed operation of a control valve according to the equation $$\text{Sample Quantity} = \text{Flow Rate} \times \text{Time}$$

Empirically obtained data stored in a microprocessor permits adjustment of the sample quantities taken by the system.

Thus, with the sampling system of the present invention, there is infinite programmability which permits any desired quantity of a sample to be taken up and dispensed into or combined with reagents. The system also permits very small quantities of a serum to be accurately and precisely dispensed. For example, in accordance with the presently preferred embodiment, sample quantities of as little as one microliter can be taken up and dispensed with a coefficient of variation of only about 0.5 percent.

The system of the present invention also permits two serum samples to be withdrawn from the specimen container simultaneously during a single cycle of the specimen container conveyor means by providing a pair of sample tubes, each of which is connected to a separate pressure-generating means. This permits a significant speed-up of the system operation when more than one test is to be performed on a particular serum.

The system of the present invention also includes a fluid-level sensing means for controlling the relative movement of the sampler assembly and the specimen container to ensure that the sample tubes are properly immersed in the serum specimen before the pressure-generating means is actuated to withdraw the sample from the specimen container. In accordance with the preferred embodiment, this is accomplished by forming the two sample tubes of electrically conductive material and connecting a source of electrical current to the tubes. A current-detecting circuit is connected between the current source and one of the sample tubes. When the tubes are properly immersed in the serum specimen, a current will flow between the sample tubes; and the current-detecting circuit will indicate that the pressure-generating means can be actuated.

The fluid-level sensing means permits the sampling system to operate effectively notwithstanding variations in the level of serum within the specimen container, and helps ensure that the sample tubes will be properly immersed in the fluid to take up the desired quantity of fluid every time.

The sampling system of the present invention thus permits very small, yet precise amounts of a serum to be taken up and dispensed accurately with a high degree of reliability. The system operates faster than most existing systems and is relatively inexpensive in construction.

Other objects and advantages of the invention will become apparent during the following description of the presently preferred embodiment taken in conjunction with the drawings.

DETAILED DESCRIPTION OF THE PREFERRED EMBODIMENT

The system of the invention was developed particularly for use in connection with an automated, chemistry-analyzing apparatus for serum analysis and, accordingly, will be described within such an environment. It should be understood, however, that it is not intended to limit the invention to such an application.

Many of the details of the automated chemistry-analyzing apparatus will not be described as they are not necessary for a clear understanding of the invention. Reference, however, is made to commonly assigned U.S. Pat. No. 3,901,656 entitled APPARATUS AND METHOD FOR PREPARING AND PRESENTING SERUM CHEMISTRIES FOR ANALYZATION for an overall description of an apparatus in which the fluid-sampling system of the present invention may be utilized.

Figure 1:
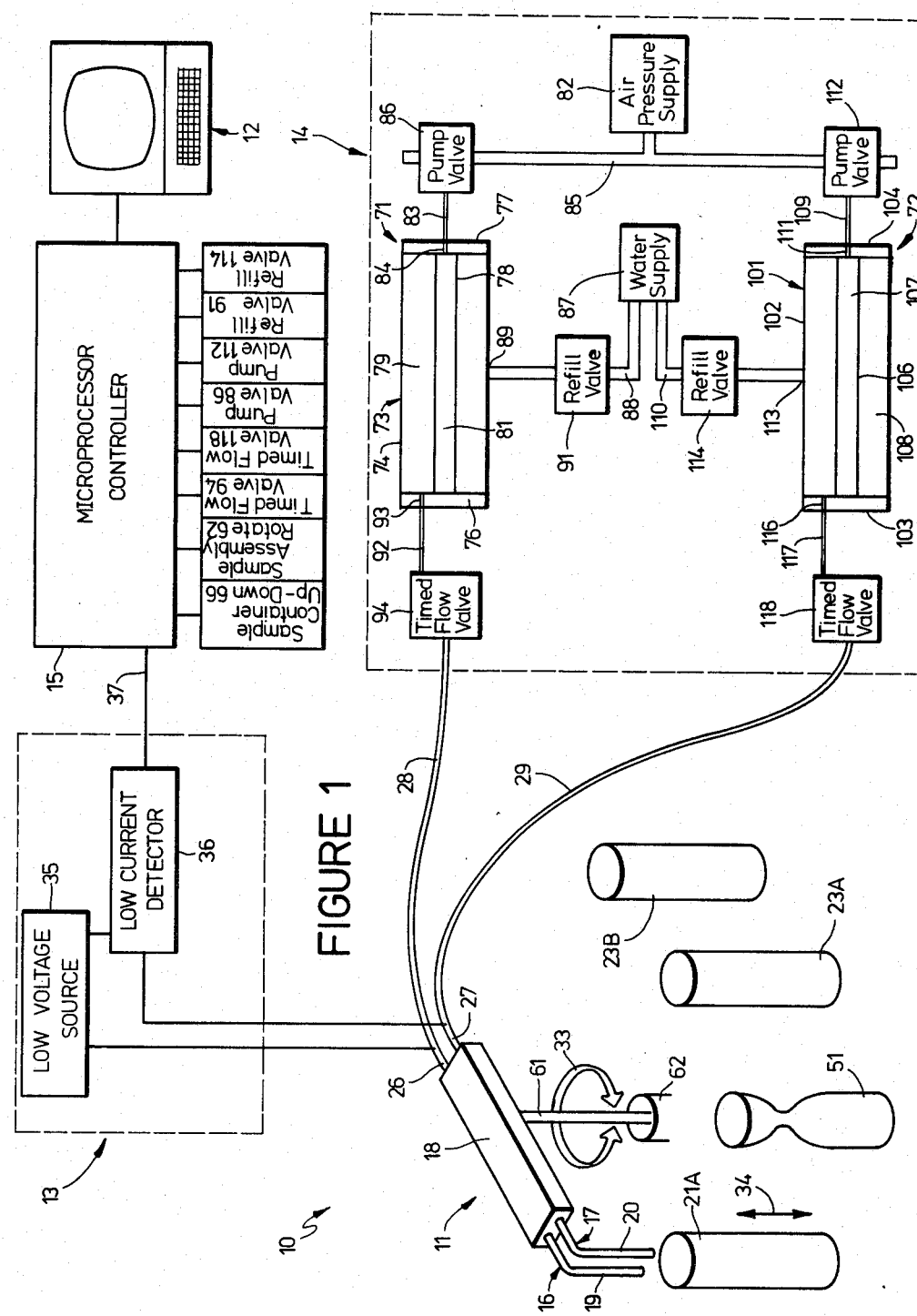
FIG. 1 schematically illustrates a fluid-sampling system according to a presently preferred embodiment of the invention.

In FIG. 1, the fluid-sampling system is generally designated by reference numeral 10 and comprises the following basic components: a sampler assembly 11 for withdrawing serum samples from a serum specimen container 21a and for dispensing the serum samples into one or both of reagent containers 23a and 23b; sampler assembly drive means 11a for moving the sampler assembly among serum withdrawal, serum dispensing and sampler assembly purging positions; information input means for entering information upon the tests to be conducted with the system and the sample quantities that are needed in the tests; serum level detecting means 13 for detecting the proper immersion of the sampler assembly into the serum specimen to be sampled; pressure-generating means 14 for withdrawing serum from specimen container 21a and dispensing it into reagent containers 23a and 23b; and a microprocessor controller 15 for controlling the overall operation of the sampling system.

Sampler assembly 11 comprises a pair of sample tubes 16 and 17 which are supported by and extend through a horizontal support housing 18. The front ends of these tubes extend outwardly from the front end of housing 18 and are bent downwardly at substantially a 90° angle to define downwardly extending portions 19 and 20 as illustrated in FIG. 1. The length of downwardly extending portions 19 and 20 is preferably approximately equal to the height of serum specimen container 21a so that they may extend fully into the container to withdraw serum samples therefrom as will be explained hereinafter.

The back ends 26 and 27 of sample tubes 16 and 17 extend outwardly from the back end of housing 18 and are connected to pressure-generating means 14 by a pair of flexible hoses 28 and 29, respectively. As will also be fully explained hereinafter, pressure-generating means 14 is designed to generate a constant negative pressure within sample tubes 16 and 17 to withdraw precise quantities of serum samples from serum specimen container 21a, and to generate a constant positive pressure within the tubes to dispense the serum samples into reagent containers 23a and 23b where they are combined with appropriate reagents to analyze the serum.

Sample tubes 16 and 17 may be formed of an electrically conductive metal and are preferably an electropolished stainless steel and, in the presently preferred embodiment, have an inside diameter of 0.016 inch. The electropolished outer surfaces of the front ends 19 and 20 of the tubes inhibit serum from sticking to the outer surfaces of the tubes when they are immersed in the serum. If non-electropolished stainless steel is used for the sample tubes, the outer surfaces of the tube ends may be coated with PTFE to inhibit serum from adhering to the tubes. Such features help prevent cross-contamination between different serum specimens being analyzed by the apparatus.

Figure 2:
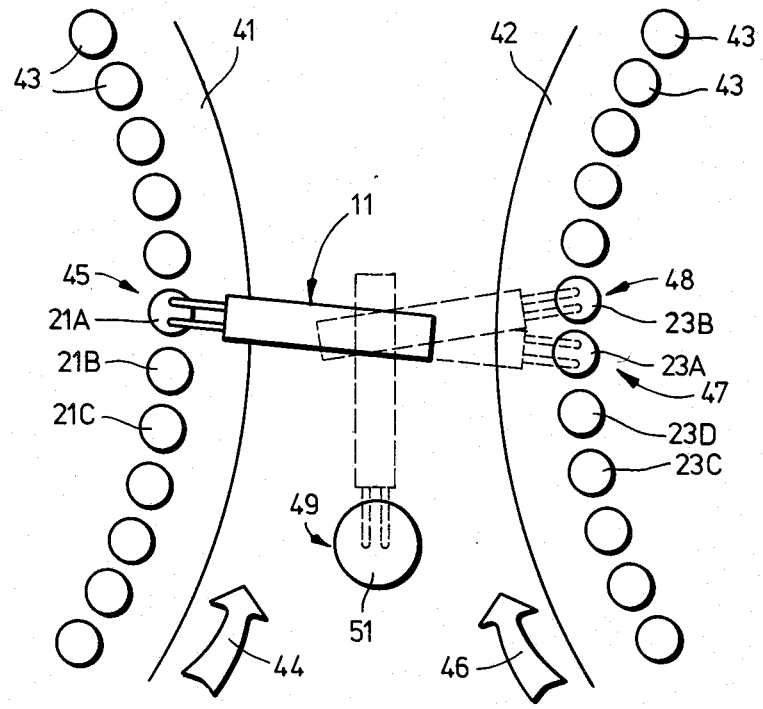
FIG. 2 schematically illustrates a top view of the sampler assembly of FIG. 1 in conjunction with container conveyor means of an automated chemistry-analyzing apparatus.

With reference now to FIG. 2, the automated chemistry-analyzing apparatus within which the fluid-sampling system of the present invention is incorporated preferably includes a pair of conveyor means 41 and 42 which can conveniently comprise a pair of rotating turntables. Each of the turntables is provided with a plurality of apertures 43 around its periphery for receiving and supporting a plurality of containers such as test tubes or the like Conveyor means 41 is adapted to carry a plurality of serum specimen containers 21a, 21b, 21c, etc., each of which may contain a different serum specimen to be analyzed. For example, one container 21a may contain a blood specimen from a first patient; another container 21b may contain a blood specimen from a second patient; a third container 21c may contain a spinal fluid specimen from a third patient; and so forth.

Conveyor means 41 is adapted to be rotated as indicated by arrow 44 by a stepping motor or the like, not shown, to sequentially move the containers, one at a time, to a serum sample withdrawal position 45, occupied in FIG. 2 by container 21a. At this position, it is aligned with sampler assembly 11 to permit the withdrawal of serum samples.

Conveyor means 42 is adapted to carry a plurality of reagent containers 23a, 23b, 23c, 23d, etc. In operation of the system, serum samples taken from the serum specimen containers 21 are dispensed into the reagent containers 23 for combination with an appropriate reagent or reagents for the tests to be performed.

The containers 23 can be empty test tubes which are moved sequentially into sample-dispensing positions 47 and 48, occupied in FIG. 2 by containers 23a and 23b. At positions 47 and 48, the containers (e.g., 23a and 23b) each receive precise quantities of a serum sample to be tested from sampler assembly 11. As conveyor 42 continues to be indexed, containers 23a and 23b will eventually reach a reagent dispensing position at which the appropriate reagent or reagents will be added to each of the containers, mixed together with the serum samples, and allowed to react to produce test chemistries which can be analyzed to ascertain the constituent of interest within each specimen.

In some applications, it is also possible that containers 23 will already contain the appropriate reagents so that the serum samples will be dispensed directly into the reagents at positions 47 and 48.

After dispensing the serum samples into reagent containers 23, sampler assembly 11 is moved to a purging position indicated by arrow 49 directly above a purge container or receptacle 51 positioned within the housing of the apparatus. The sampler tubes are thoroughly cleaned at the purging position by a cleansing liquid (i.e., deionized water) to remove any serum that may be remaining in the sample tubes 16 and 17 to prevent any cross-contamination between serum samples. At this position also, the sample tubes are filled with deionized water as will be explained hereinafter.

Figure 3:
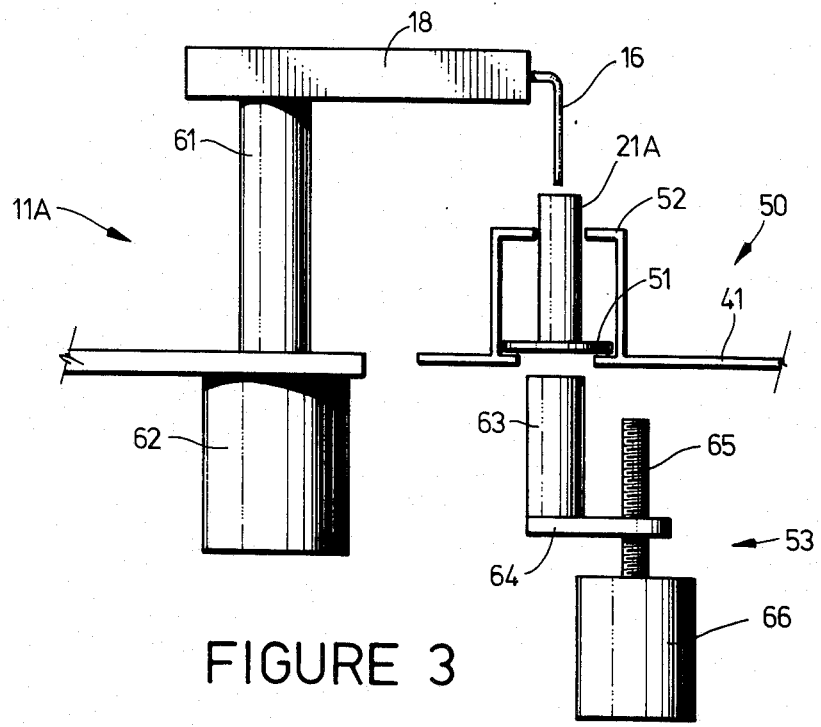
FIG. 3 schematically illustrates the details of the sampler assembly drive means of FIG. 1.

FIG. 3 schematically illustrates a system for immersing the sample tube into the serum sample. Such a system provides relative motion between the outer ends 19 and 20 of sampler tubes 16 and 17 and the specimen container 21.

As shown in FIG. 3, sampler assembly housing 18 is mounted on a shaft 61 which is connected to the rotating shaft of a stepping motor 62. Actuation of stepping motor 62 will cause shaft 61 and, hence, sampler assembly housing 18 to be rotated horizontally among the serum withdrawal position (shown in FIG. 2) and the serum dispensing and sampler assembly purging positions (shown in phantom lines in FIG. 2).

A specimen container moving means 50 can be provided for raising the specimen container at the serum withdrawal position 45 so that the sample tubes are immersed in the serum sample. One drive means 50 permitting such relative motion between the sample tubes and serum sample can include at each station of conveyor 41 a freely liftable platform 51 and a guide (or guides) 52. The specimen containers 21 are carried by conveyor 41 on the platforms 51. Means 53 to lift the platforms 51 can be mounted below the conveyor 41 at the serum withdrawal position 45. Means 53 includes a shaft 63, that is driven up and down by the follower or nut 64 of a ball screw 65. The ball screw 65 is driven by a stepping motor 66 to move platform 51 and specimen container 21a up and down with shaft 63.

As indicated previously, and with reference to FIG. 1, pressure-generating means 14 is coupled to sample tubes 16 and 17 for the withdrawal of serum samples from serum specimen containers 21 and for dispensing of said serum samples into reagent containers 23. More specifically, pressure-generating means 14 comprises first and second pressure-generating means 71 and 72 which are connected to sample tubes 16 and 17, respectively, via flexible hoses 28 and 29, respectively.

First pressure-generating means 71 includes a first Bourdon pump 73 which comprises an elongated, cylindrical-shaped vessel 74 having a rigid, substantially non-deformable, outer wall and which is closed at either end by closure members 76 and 77 to provide a water-tight and air-tight container. A hollow, flexible, tubular-shaped Bourdon tube 78 is supported within pump 73 and extends axially therethrough from end closure 76 to end closure 77 to define an annular chamber 79 within cylindrical vessel 74 surrounding tube 78. Bourdon tube 78 is attached to the ends 76 and 77 in such a way as to ensure that annular chamber 79 will be isolated from interior chamber 81 within tube 78.

Chamber 81 within tube 78 is coupled to an air pressure source 82 via an air flow line 83 connected to orifice-defining means 84 extending through end closure member 77. Preferably, the air pressure source is adapted to supply a substantially constant pressure of 30 p.s.i. to the interior of the Bourdon tubes 78 and 106. A three-way pump valve 86 is positioned in flow line 83 to control the flow of air into and out of Bourdon tube chamber 81 as will be explained here- inafter.

Annular chamber 79 is coupled to a supply of deionized water 87 by a water flow line 88 connected to an orifice-defining means 89 provided in the sidewall of vessel 74. A refill valve 91 is provided in water flow line 88 to control the flow of water from supply 87 to annular chamber 79.

Annular chamber 79 is also coupled to sample tube 16. Specifically, one end of a conduit 92 is coupled to annular chamber 79 via an orifice-defining means 93 in end closure 76, while the opposite end of the conduit is connected to a timed flow valve 94. Flexible hose 28 connects the valve 94 to the back end 26 of sample tube 16.

Second pressure-generating means 72 is essentially identical to first pressure-generating means 71. It includes a Bourdon pump 101 which comprises an elongated, cylindrical-shaped vessel 102 having a rigid outer wall, end closure members 103 and 104, and a hollow, axially extending, flexible Bourdon tube 106 having an interior chamber 107 and defining an annular chamber 108 therearound.

Chamber 107 is coupled to the air pressure source 82 via air flow line 109 connected to orifice-defining means 111 in end closure 104, and a three-way pump valve 112 is positioned in flow line 109 to control the flow of air into and out of Bourdon tube chamber 107.

Annular chamber 108 is coupled to deionized water supply 87 by water flow line 110 connected to orifice-defining means 113 in the sidewall of cylindrical vessel 102, and refill valve 114 is provided in water flow line 110 to control the flow of water into annular chamber 108.

Annular chamber 108 is connected to the back end 27 of sample tube 17 via orifice-defining means 116 in end closure 103, pipe 117, timed flow valve 118, and flexible hose 29.

Pressure-generating means 71 and 72 are independently controllable by microprocessor controller 15, and are provided so that two samples of a particular serum specimen may be simultaneously withdrawn from a serum specimen container during one cycle of the specimen container conveyor means 41 (FIG. 2). This is an important capability in that it permits a significant reduction in time in those situations wherein more than one test is to be performed on a particular specimen and more than one sample of the serum is needed. In currently available systems, only one serum sample can be withdrawn from a serum specimen container per cycle of the specimen container conveyor means; and it is necessary to wait until the desired specimen container has returned to the serum sample withdrawal position before a second sample can be withdrawn.

The present invention permits two very small, yet very precise, and different quantities of a serum sample to be withdrawn from a specimen container and dispensed into separate reagent containers so that two separate tests can be performed on the serum. The attainment of this high precision with only small quantities of serum is achieved by the use of Bourdon pumps 73 and 101 in conjunction with the timed flow valves 94 and 118 which can very precisely control the withdrawal and dispensing of serum by sampler assembly 11. Although, as was indicated previously, the use of a Bourdon pump in a fluid-sampling system is known and has been taught in commonly assigned U.S. patent application Ser. No. 304,384, that application teaches the use of a Bourdon pump to take up and dispense one of a plurality of specific, finite increments of fluid. The present invention, on the other hand, permits infinitely variable sample quantities to be withdrawn from the serum specimen container and dispensed into the reagent containers. It achieves this by generating a substantially constant positive and a substantially constant negative pressure within the sample tubes 16 and 17. The quantities of serum sample to be taken up and dispensed are determined by the fluid mechanics of the sampling system and its effect on flow rate and by the timed operation of timed flow valves 94 and 118 according to the equation Sample Quantity = Flow Rate × Time.

Empirically obtained data stored in microprocessor controller 15 permits automatic adjustment of the sample quantities to be taken by the sample tubes depending on the particular test to be performed. Specifically, by merely controlling the time that timed flow control valves 94 and 118 are opened, precise quantities of a specimen sample can be taken up by sample tubes 16 and 17 and dispensed. Since valves 94 and 118 are independently controllable, different quantities of a serum can be picked up simultaneously by the sample tubes 16 and 17. The system may be programmed so that the operator may enter the sample quantity needed for each test to be performed with the information entry means 12 and the microprocessor controller 15 will select the operating times of the valves 94 and 118 from empirical data stored within its memory and operate the timed control values through suitable output transducers.

A clearer understanding of the operation of the pressure-generating means 14 of the invention may be understood from the step-by-step operation of the overall fluid-sampling system as it may be used in an automated chemistry-analyzing apparatus.

Figure 4:
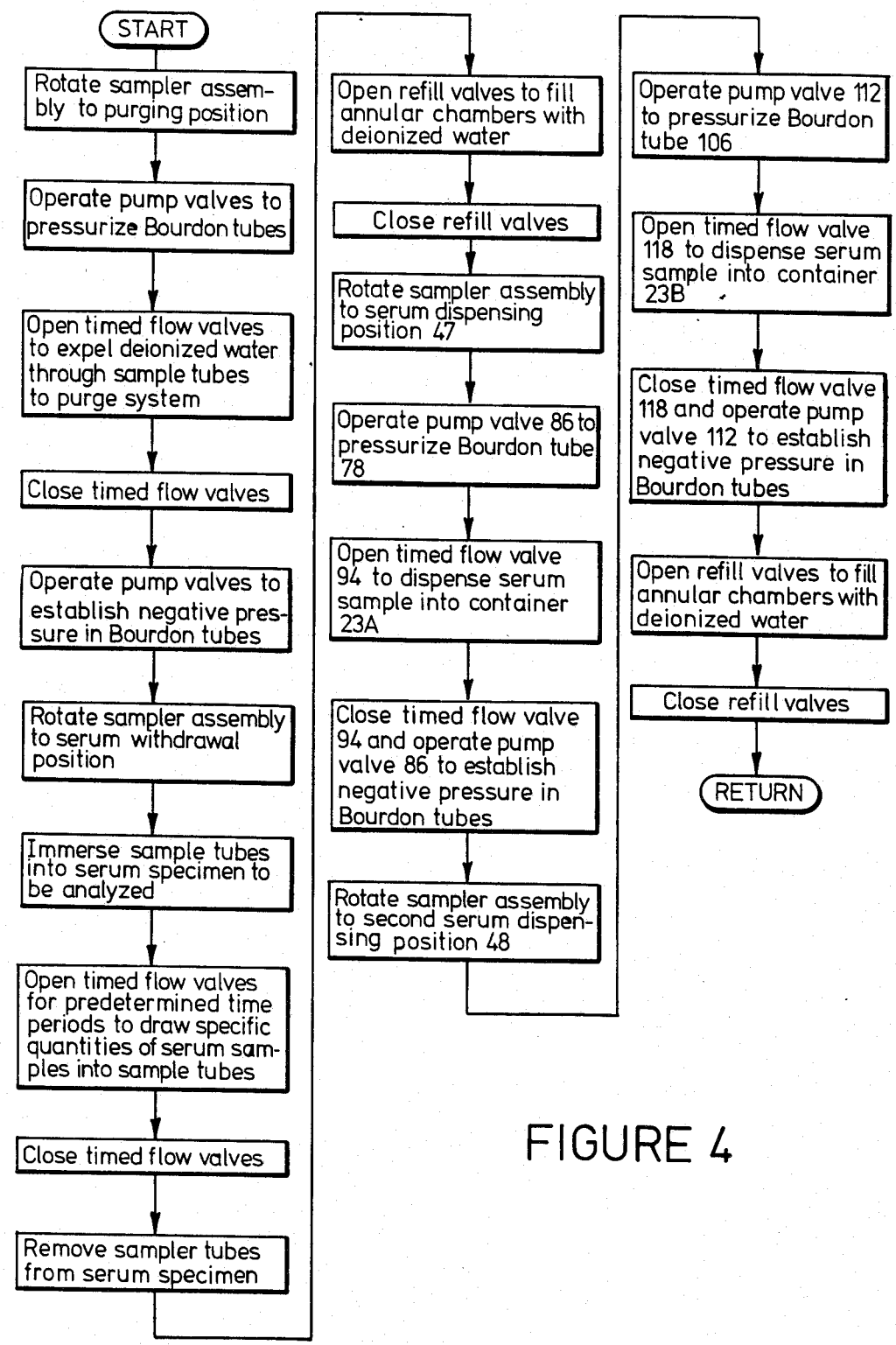
FIG. 4 is flow chart to help explain the overall operation of the fluid-sampling system of the present invention.

Reference is made to FIG. 4 which is a flow chart illustrating each of the steps to be performed by the system. Initially, it will be assumed that the sampler assembly has just dispensed samples of a serum into one or more reagent containers 23. Therefore, sampler assembly 11 will be positioned in either serum-dispensing position 47 or serum-dispensing position 48 (FIG. 2). Before the sample tubes can be used to receive new serum samples, it is necessary that they be cleaned to avoid any chances of cross-contamination between different serums. Therefore, as the first step in the operation of the system, stepping motor 62 (FIG. 3) is actuated to rotate the sampler assembly 11 to sampler assembly purging position 49 where the sample tubes 16 and 17 will be positioned above purge container 51. When the sampler assembly 11 reaches purging position 49, stepping motor 62 is stopped and pump valves 86 and 112 are actuated to pressurize the interior chambers 81 and 107 of Bourdon tubes 78 and 106 from 30 p.s.i. air pressure supply 82. Specifically, the interior chambers of tubes 78 and 106 are pressurized such that the walls of the tubes will tend to push outwardly against the deionized water that fills the annular chambers 79 and 108. It should be emphasized that pump valves 86 and 112 simply function to allow compressed air into the Bourdon tubes. They are not used for metering purposes. In the present invention, metering is accomplished only through timed flow valves 94 and 118 as will be explained hereinafter.

After the Bourdon tubes are pressurized, timed flow valves 94 and 118 are opened. Upon opening the valves 94 and 118, the air pressure within chambers 81 and 107 causes the walls of Bourdon tubes 78 and 106 to expand and force deionized water out of annular chambers 79 and 108 through orifice-defining means 93 and 116. This forces the water in pipes 92 and 117, hoses 28 and 29, and sample tubes 16 and 17 outwardly to expel water out of sample tubes 16 and 17 into the purge container 51. Water is continued to be expelled through the system for a sufficient period of time to clean the interior walls of sample tubes 16 and 17 of any serum that may have adhered thereto from the previous sampling operation. Timed flow valves 94 and 118 are then closed to stop the flow of water.

Pump valves 86 and 112 are then operated so that the Bourdon tubes will thus be vented to atmosphere. This releases the positive pressure in tubes 78 and 106 causing the tubes to relax and establish a negative pressure of six inches of water within the chambers 79 and 108.

Stepping motor 62 is then again actuated to rotate sampler assembly 11 to serum withdrawal position 45 where it is aligned with a serum specimen container 21a containing a serum to be analyzed. Stepping motor 66 is then actuated to lift shaft 63 and raise the specimen container 21a to immerse the ends 19 and 20 of the sample tubes 16 and 17 into the container 21a and into the serum contained therein. The shaft 63 will continue to raise the specimen container 21a until serum level detecting means 13 determines that the ends of the sample tubes are immersed in the serum contained within specimen container 21a.

Specifically, the electrically conductive tubes 16 and 17 are coupled to a low voltage source 35 (e.g., a millivolt alternating current potential source) to define an electrical circuit which is normally open due to the gap between the ends 19 and 20 of the two tubes. When, however, the ends of the tubes contact the serum in the container, the serum will close the electrical circuit therebetween and a small amount of current will flow in the circuit. When low current detector circuit 36, connected between source 35 and one of the sample tubes, detects this current flow, a stop signal will be produced on line 37 which will cause the microprocessor controller 15 to stop the downward movement of shaft 63 by stopping the rotation of stepping motor 66 and ball screw 65. The low current detector 36 may be a semiconductor switching circuit to provide a voltage level change as a signal to the microprocesser controller. Such circuits are well known in the electrical control art.

This level-detecting capability is an important feature of the present invention in that it ensures that the ends of the sample tubes will be properly immersed in the serum specimen to be sampled irrespective of the quantity of serum placed into or remaining in the serum specimen containers 21. This makes it unnecessary to control the level of the serum placed in the serum specimen containers 21 as the system will operate effectively whether the containers are substantially full or nearly empty.

When it is determined that the ends of sample tubes 16 and 17 are properly immersed in the serum specimen to be sampled, timed flow valves 94 and 118 are then opened for predetermined time periods under control of the microprocessor controller 15. The negative pressure within the chambers 79 and 108 from the relaxation of the walls of the tubes 78 and 106 will cause quantities of serum samples to be drawn into the sample tubes 16 and 17. The quantity of serum drawn into each of the sample tubes is a function only of the mechanics of flow through the system and the duration of time that the timed flow valves 94 and 118 are left open. Since the only variable in this equation is the time that the valves are left open, the quantity of serum drawn into each sample tube can be very precisely controlled, even when only very small quantities of serum are drawn into the tubes.

After precise quantities of serum have been drawn into each of the two tubes 16 and 17 (since the timed flow valves 94 and 118 are independently controllable by controller 15, a different quantity can be drawn into each tube depending on how much is needed for each test to be performed), timed flow valves 94 and 118 are closed; and the specimen container is lowered by again actuating stepping motor 66 to lower shaft 63. Refill valves 91 and 114 are then opened to refill the annular chambers 79 and 108 with deionized water from water supply 87 and are then closed.

Thereafter, stepping motor 62 is again actuated to rotate the sampler assembly 11 to dispensing position 47 wherein sample tubes 16 and 17 are aligned with container 23a. Pump valve 86 is then operated to pressurize Bourdon tube 78. Pump valve 112 is, optionally, not operated at this time. Timed flow valve 94 is then opened for a predetermined period of time to cause the sample taken up by sample tube 16 to be expelled into container 23a due to the positive pressure within the tube 78 forcing water out of annular chamber 79.

In order to ensure that only serum and not deionized water will be dispensed into the reagent containers 23a and 23b, it is preferable that slightly larger quantities of serum samples be withdrawn from container 21a than are actually required for the particular tests to be performed and are to be dispensed into containers 23a and 23b. The slight amount of serum left in the sample tubes will be flushed out during the above-described purging step.

After the correct time period as determined by microprocessor controller 15, timed flow valve 94 is closed; and pump valve 86 is opened to atmosphere. Motor 62 is actuated to rotate sampler assembly 11 to dispensing position 48 wherein the sample tubes are aligned with reagent container 23b. When it reaches this position, pump valve 112 is operated to pressurize Bourdon tube 106. Timed flow valve 118 is then opened to expel the serum sample held in sample tube 17 into container 23b; and after a precise period of time, as determined by controller 15, timed flow valve 118 is closed, and pump valve 112 is opened to atmosphere. Chambers 79 and 108 are at a negative pressure. Refill valves 91 and 114 are again opened to refill annular chambers 79 and 108 with deionized water. Refill valves 91 and 114 are then closed.

The sampler assembly is then ready to be rotated back to the purging position 49, and the entire operation may be repeated to test the next serum specimen in container 21b. In this regard, the microprocessor controller 15 also controls conveyor means 41 and 42 so that after serum samples have been withdrawn from specimen container 21a and dispensed into reagent containers 23a and 23b, the conveyor means will be actuated to rotate specimen container 21b to the serum withdrawal position 45 and reagent containers 23c and 23d to serum-dispensing positions 47 and 48, respectively. It should also be understood that it is not necessary that both sample tubes 16 and 17 be used to pick up serum samples at any particular time. If only one test is to be performed on a particular serum, only one of the sample tubes, for example, sample tube 16, and only one of the pressure-generating means 71 or 72 need be actuated to take up a serum sample from a container. In such a situation, it will only be necessary for the sampler assembly to be rotated to one of the serum-dispensing positions to dispense serum into a reagent container.

Where sampling speed is important, the pump valves 86 and 112 are preferably operated simultaneously, even in instances where only a single sample is desired to be taken up by only one of the sample tubes. Alternatively, a single pump valve may be used to connect Bourdon pumps 71 and 72 to air pressure supply 82. It is the actuation of either or both of the timed flow valve that determines fluid flow through the sample tubes for sampling, dispensing, and purging purposes.

The microprocessor controller 15 controls essentially the entire overall operation of the fluid-sampling system as indicated above and as shown in FIG. 1. It controls the operation of each of the valves in the system as well as the rotational movement of the sampler assembly and the up and down movement of the specimen container. As indicated, the operating times of the timed control valves 94 and 118, which effect control of the sample quantities dispersed for testing purposes, are determined by the microprocessor from data stored in its memory. There are many types of microprocessors available that would be suitable for use in the present invention, for example, Intel Model 8085 Microcomputer may be used.

While a presently most preferred embodiment of the invention has been described, it should be clearly understood that the invention could take many other forms. For example, although described primarily in connection with a chemistry-analyzing apparatus for analyzing serum samples, the invention can also be used in a number of other applications in which a fluid-sampling capability is required. It is also possible, if desired, to employ more than two sample tubes and associated pressure-generating means with the system. Because the invention can take a variety of other forms, it should be understood that it is to be limited only by the scope of the following claims.

We claim:

1. A fluid-sampling system comprising:
   means for collecting and dispensing serum samples having precise quantities, including,
   a sampler assembly including two sample tubes;
   means for generating positive and negative pressures in said two sample tubes; and
   control means for generating a negative pressure in said two sample tubes for withdrawing fluid samples from one of a plurality of containers into said two sample tubes and for generating a positive pressure in said two sample tubes for dispensing said fluid samples from said two sample tubes into others of said plurality of containers.

2. A fluid-sampling system as recited in claim 1 wherein said control means includes means for generating a positive pressure in the first of said two samples tubes for dispensing the fluid sample therein into a second container, and for generating a positive pressure in the second of said two sample tubes for dispensing the fluid sample therein into a third container.

3. A fluid-sampling system as recited in claim 2 and further including drive means for immersing said two sample tubes into the fluid samples in the one container to permit a fluid sample to be withdrawn therefrom, and for thereafter removing said two sample tubes out of said one container.

4. A fluid-sampling system as recited in claim 3 and further including fluid-level sensing means for detecting when said two sample tubes are immersed in the fluid to be sampled in said one container.

5. A fluid-sampling system as recited in claim 4 wherein said two sample tubes are formed of electrically conductive material, and wherein said fluid-level sensing means includes a source of electrical current electrically connected with said two sample tubes, and a current-detecting circuit connected between said source of current and one of said sample tubes, said control means being connected to said current-detecting circuit and said drive means for terminating the relative motion between said two sample tubes and said fluid sample when said current detecting circuit detects a current indicating that said two sample tubes are immersed in said fluid sample.

6. A fluid-sampling system as recited in claim 5 wherein said source of electrical current comprises a millivolt alternating current potential source.

7. A fluid-sampling system as recited in claim 2 wherein said pressure-generating means includes first means for generating positive and negative pressures in the first of said two sample tubes and second means for generating positive and negative pressures in the second of said two sample tubes, and wherein said control means includes means for independently controlling said first and second pressure-generating means.

8. A fluid-sampling system as recited in claim 7 wherein said first and second pressure-generating means include first and second Bourdon pump means connected to said first and second sample tubes, respectively, for establishing a substantially constant positive and a substantially constant negative pressure within each of said first and second sample tubes, and first and second timed control valve means connected between said first and second Bourdon pump means and said first and second sample tubes, respectively, and operable by said control means for generating said substantially constant positive or constant negative pressure in said first and second sample tubes for precise periods of time for withdrawing precise fluid sample quantities from said one container into said first and second sample tubes, and for dispensing precise fluid sample quantities from said first and second sample tubes into said second and third containers, respectively.

9. A fluid-sampling system as recited in claim 8 wherein said first and second timed control valve means are independently controllable by said control means for independently controlling the precise fluid sample quantity withdrawn into and dispensed from each of said first and second sample tubes.

10. A fluid-sampling system as recited in claim 9 wherein said means for establishing a substantially constant positive or constant negative pressure includes a pressure source connected to said first and second Bourdon pump means for establishing a constant positive pressure in said first and second Bourdon pump means.

11. A fluid-sampling system as recited in claim 1 wherein said fluid samples comprise serum samples.

12. A fluid-sampling system comprising:
    a sample tube;
    means for generating substantially constant positive and constant negative pressures in said sample tube; and
    control means connected to said pressure-generating means for generating a substantially constant negative pressure in said sample tube for a first predetermined period of time for withdrawing a first precise quantity of a fluid sample from a first container, and for generating a substantially constant positive pressure in said sample tube for a second predetermined period of time for dispensing a second precise quantity of said fluid sample from said sample tube into a second container.

13. A fluid-sampling system as recited in claim 12 wherein said pressure-generating means comprises Bourdon pump means connected to said sample tube for establishing a constant positive or a constant negative pressure, and timed control valve means connected between said Bourdon pump means and said sample tube and operable by said control means for generating said constant negative pressure in said sample tube for said first predetermined period of time and for generating said constant positive pressure in said sample tube for said second predetermined period of time.

14. A fluid-sampling system as recited in claim 13 wherein said Bourdon pump means includes:
    an elongated, flexible Bourdon tube centrally supported within a surrounding vessel to define an annular chamber around said Bourdon tube, said annular chamber being connected to said sample tube through said timed control valve;
    a liquid source in communication with said annular chamber through a refill valve for maintaining said annular chamber filled with said liquid;
    a pressure source in communication with the interior of said Bourdon tube through a three-way pump valve having one position connecting said positive pressure source to the interior of said Bourdon tube and a second position opening the interior of said Bourdon tube to atmosphere; and wherein
    said control means includes means for positioning said three-way valve to said second position for opening the interior of said Bourdon tube to atmosphere and to relax said Bourdon tube to generate said constant negative pressure in said sample tube for withdrawing said first precise quantity of fluid, said timed flow valve being opened thereafter to cause said liquid in said sample tube to flow toward said annular chamber and for positioning said three-way valve to said first position for opening the interior of said Bourdon tube to said constant positive pressure source to establish said positive pressure therein tending to urge the walls said Bourdon tube outwardly, said timed flow valve being opened thereafter to cause said liquid in said annular chamber to flow toward said sample tube dispensing said second precise quantity of fluid.

15. A fluid-sampling system as recited in claim 14 wherein said liquid comprises deionized water.

16. A fluid-sampling system as recited in claim 12 wherein said fluid sample comprises a serum sample.

17. The fluid-sampling system of claim 12, comprising:
two sample tubes and wherein said means for generating essentially constant positive and negative pressures generate substantially constant negative pressures in said two sample tubes for predetermined periods of time to withdraw precise quantities of fluid samples from the first container into the sample tubes and generate substantially constant positive pressures in the two samples tubes for second predetermined periods of times for dispensing precise quantities of fluid samples from said two sample tubes into other containers.

18. A fluid-sampling system for an automated, chemistry-analyzing apparatus for serum analysis comprising:
a specimen container containing a serum specimen to be tested, said speciment container being supported in a serum withdrawal position;
first and second reagent containers for receiving serum samples to be mixed with one or more reagents for testing, said first and second reagent containers being supported in first and second serum-dispensing positions, respectively;
a sampler assembly including two sample tubes;
drive means for immersing said sample tubes in said serum specimen to be tested, for removing said sample tubes from said serum specimen to be tested, and for moving said sampler assembly among said serum withdrawal position and said first and second serum-dispensing positions;
means for generating positive and negative pressures in said two sample tubes; and
control means connected to said pressure-generating means for generating a negative pressure in said two sample tubes for withdrawing serum samples from said specimen container into said two sample tubes, for generating a positive pressure in the first of said sample tubes for dispensing the serum sample therein into said first reagent container, and for generating a positive pressure in the second of said two sample tubes for dispensing the serum sample therein into said second reagent container.

19. A fluid-sampling system as recited in claim 18 wherein said control means includes means for generating a negative pressure in said first and second sample tubes for first and second predetermined periods of time, respectively, to withdraw first and second predetermined quantities of serum sample from said specimen container, respectively, and for generating a positive pressure in said first and second sample tubes for third and fourth predetermined periods of time, respectively, to dispense third and fourth quantities of serum sample into said first and second reagent containers, respectively.

20. A fluid-sampling system as recited in claim 19 wherein said control means includes means for simultaneously generating said negative pressure in said first and second sample tubes.

21. A fluid-sampling system as recited in claim 19 wherein said pressure-generating means includes first and second Bourdon pump means connected to said first and second sample tubes, respectively; means for operating said first and second Bourdon pump means to establish a constant positive or a constant negative pressure in said first and second sample tubes, and first and second timed control valve means connected between said first and second Bourdon pump means and said first and second sample tubes, respectively, and operable by said control means, for generating said negative pressure in said first and second sample tubes for said first and second predetermined periods of time, respectively, and for generating said positive pressure in said first and second sample tubes for said third and fourth predetermined periods of time, respectively.

22. A fluid-sampling system as recited in claim 21 wherein said first and second Bourdon pump means each include:
an elongated, flexible, Bourdon tube centrally supported within a surrounding vessel to define an annular chamber around said Bourdon tube, said annular chamber being connected to said sample tube through said timed control valve;
a liquid source in communication with said annular chamber through a refill valve for maintaining said annular chamber filled with said liquid;
a substantially constant positive pressure source in communication with the interior of said Bourdon tube through a three-way pump valve having one position connecting said positive pressure source to the interior of said Bourdon tube and a second position opening the interior of said Bourdon tube to atmosphere; and wherein
said control means includes means for positioning said three-way valve to said second position for opening the interior of said Bourdon tube to atmosphere to relax said Bourdon tube, said timed flow valve being opened thereafter to cause said liquid in said sample tube connected thereto to flow toward said annular chamber, and for positioning said three-way valve to said first position for connecting the interior of said Bourdon pump to said substantially constant positive pressure source to establish said positive pressure therein tending to urge the walls said Bourdon tube outwardly, said timed flow valve being opened thereafter to cause said liquid in said annular chamber to flow toward said sample tube.

23. A fluid-sampling system as recited in claim 18 and further including a purge container supported in a purging position, and wherein said drive means further includes means for moving said sampler assembly to said purging position after said serum samples are dispensed into said first and second reagent containers, and wherein said system further includes means for purging said first and second sample tubes at said purging position for removing serum remaining within said first and second sample tubes.

24. A fluid-sampling system as recited in claim 23 wherein said purging means includes a source of cleansing fluid connected to said first and second sample tubes.

25. A fluid-sampling system as recited in claim 18 and further including serum specimen level sensing means for detecting when said first and second sample tubes are immersed in said serum specimen by relative movement initiated by the drive means, and wherein said control means is connected with said serum specimen level sensing means and said drive means for terminating the relative movement between said sampler assembly and specimen container when said serum specimen level sensing means detects that said first and second sample tubes are immersed in said serum specimen.

26. A fluid-sampling system as recited in claim 25 wherein said first and second sample tubes are formed of electrically conductive material, and wherein said serum specimen level sensing means includes a source of electrical current electrically connected with said first and second sample tubes, and a current-detecting circuit connected between said source of current and one of said sample tubes, said control means being connected with said current-detecting circuit and said drive means for terminating the motion of said first and second sample tubes into said serum specimen to be sampled when said current-detecting circuit detects a current indicating that said first and second sample tubes are immersed in said serum specimen to be sampled.

27. A system for sampling serum, comprising:
a first conveyor means to move a plurality of specimen containers to a serum-wthdrawal position;
a second conveyor means to move a plurality of reagent containers to a serum-dispensing position;
a serum sampler tube adapted to be moved between the serum-withdrawal position and the serum-dispensing position;
means for moving said serum sample tube between the serum-withdrawal position and the serum-dispensing position;
a fluid-delivery system comprising a pressure-generating means connected with said serum-sampling tube through a timeable control valve for applying a positive and negative pressure to the serum sampler tube to dispense and withdraw serum; and
control means for said system, comprising a microprocessor including means for storing a plurality of predetermined times that correspond to quantities of serum dispensable by said sampler tube and fluid-delivery system with said positive pressure applied, means for entering a serum sample quantity and for selecting from said storage means the time corresponding to said selected serum sample quantity, means for controlling the pressure-generating means and timeable control valve of the fluid delivery system to apply negative pressure to the serum sampler tube to effect withdrawal of serum and to apply positive pressure to said serum sampler tube for said time to effect dispensing of said selected sample quantity, and means for operating said moving means to position the serum sampler at said serum-withdrawal position for withdrawal of serum and to position said serum sampler tube at the serum-dispensing position to dispense the selected serum sample.

28. The system of claim 27 wherein
said serum-sampler tube is carried by a serum-sampler assembly as one of a plurality of serum-sampler tubes and further including a plurality of fluid-delivery systems, each serum-sampler tube being connected with a separate fluid-delivery system, and wherein
the system further includes a source of potential connected to the plurality of serum-sampler tubes to apply said potential between at least two of said serum-sampler tubes and a current-detecting circuit to detect current flow from said potential source, and wherein
said system includes means to cause relative motion between the plurality of serum-sampler tubes and the specimen containers, and wherein
said microprocessor includes means for controlling the relative motion of said serum-sampler tubes and specimen containers at the serum-withdrawal position, said controlling means being connected with the current-sensing circuit to stop the relative motion between the plurality of serum-sampler tubes and specimen container at a predetermined level of current from the potential source.

29. The system of claim 28 wherein the plurality of fluid-delivery systems have substantially the same resistance to fluid flow, said microprocessor means for selecting a serum-sample quantity is adapted to permit the selection and entry of a serum-sample quantity for each of the plurality of serum-sampler tubes, and said means for controlling the fluid-delivery system is adapted to control each of the fluid-delivery systems to effect withdrawal of serum into each of the plurality of serum-sampler tubes and to select from said storage means the time corresponding to the selected serum-sample quantity for each serum-sample tube and to effect dispensing of the selected serum-sample quantity from each of the serum-sampler tubes.

30. A fluid-sampling system as recited in claim 26 wherein at least a portion of the outer surfaces of each of said first and second sample tubes are electropolished stainless steel.

31. A method comprising sampling specimens by,
causing motion to immerse a pair of small metal tubes in a fluid specimen to be sampled;
applying a potential source to the pair of metal tubes;
sensing the electrical current drawn from the potential source; and
terminating the motion when a current is sensed, said electrical current flowing between said pair of metal tubes upon their immersion in said fluid specimen.

32. A method as recited in claim 31 and further including the step of withdrawing fluid samples from said fluid specimen into said pair of metal tubes after the motion is terminated.

33. A method as recited in claim 32 wherein said withdrawing step comprises the step of applying a constant negative pressure to each of said pair of metal tubes for a predetermined period of time for withdrawing precise quantities of fluid into each of said metal tubes.

34. A method as recited in claim 33 wherein said withdrawing step further comprises the steps of applying a constant negative pressure to one of said pair of tubes for a first predetermined period of time for withdrawing a first precise quantity of fluid into said one metal tube, and for applying a constant negative pressure to the other of said pair of tubes for a second predetermined period of time for withdrawing a second precise quantity of fluid into said other metal tube.

35. A method as recited in claim 34 and further including the steps of thereafter causing motion to remove the pair of small metal tubes from the fluid specimen and to relocate the small metal tubes at a specimen dispensing station, and applying a constant positive pressure to said one and other metal tubes for third and fourth predetermined periods of time, respectively, for dispensing third and fourth precise quantities of fluid therefrom.

36. A method as recited in claim 35 and further including the step of applying a constant positive pressure to said one and other metal tubes for dispensing cleansing fluid therefrom for cleaning the interior of said one and other metal tubes.

37. A fluid-sampling system, comprising:
   a sampler assembly including a pair of metal tubes;
   means for causing motion to immerse the pair of metal tubes into a fluid specimen to be sampled;
   means for applying a potential source to the pair of metal tubes;
   means for sensing the electrical current drawn from the potential source; and
   means for terminating the motion when a current is sensed between said metal tubes.

* * * * *

UNITED STATES PATENT AND TRADEMARK OFFICE
CERTIFICATE OF CORRECTION

PATENT NO. : 4,615,866

DATED : OCTOBER 7, 1986

INVENTOR(S) : DAVID D. HYDE AND JAMES R. STUART

It is certified that error appears in the above-identified patent and that said Letters Patent is hereby corrected as shown below:

In col. 2, line 4, delete "are" and insert -- is -- therefor.

In col. 3, line 38, before "flow chart", insert -- a --.

In col. 4, line 56, after the work "like", insert -- . --.

In col. 6, line 28, delete "here- inafter" and insert -- hereinafter -- therefor.

In col. 10, line 41, delete "valve" and insert -- valves -- therefor.

In col. 11, line 19, delete "samples" and insert -- sample -- therefor.

In col. 13, line 8, before "said", insert -- of --; line 26, delete "samples" and insert -- sample -- therefor; and line 34, delete "speciment" and insert -- specimen -- therefor.

In col. 14, line 53, before "said", (first occurrence) insert -- of --.

UNITED STATES PATENT AND TRADEMARK OFFICE
CERTIFICATE OF CORRECTION

PATENT NO. : 4,615,866

DATED : OCTOBER 7, 1986

INVENTOR(S) : DAVID D. HYDE and JAMES R. STUART

It is certified that error appears in the above-identified patent and that said Letters Patent is hereby corrected as shown below:

In col. 16, line 22, delete "have", and insert -- has-- therefor.

Signed and Sealed this

Sixth Day of January, 1987

Attest:

DONALD J. QUIGG

Attesting Officer

Commissioner of Patents and Trademarks